(12) United States Patent
Futatsugi (10) Patent No.: US 7,074,181 B2
(45) Date of Patent: Jul. 11, 2006

(54) HERMETICALLY SEALED ENDOSCOPE IMAGE PICK-UP DEVICE

(75) Inventor: Yasuyuki Futatsugi, Hachioji (JP)

(73) Assignee: Olympus Corporation, Tokyo (JP)

( * ) Notice: Subject to any disclaimer, the term of this patent is extended or adjusted under 35 U.S.C. 154(b) by 103 days.

(21) Appl. No.: 10/791,455

(22) Filed: Mar. 2, 2004

(65) Prior Publication Data

US 2004/0176661 A1 Sep. 9, 2004

(30) Foreign Application Priority Data

Mar. 6, 2003 (JP) .............................. 2003-060155

(51) Int. Cl.
  *A61B 1/00* (2006.01)
  *A61B 1/04* (2006.01)

(52) U.S. Cl. ...................... 600/129; 600/110; 600/130

(58) Field of Classification Search ................ 600/109, 600/110, 129, 133; 348/75–76
See application file for complete search history.

(56) References Cited

U.S. PATENT DOCUMENTS

| | | | |
|---|---|---|---|
| 4,677,471 A * | 6/1987 | Takamura et al. ............. | 348/76 |
| 4,773,396 A * | 9/1988 | Okazaki ..................... | 600/109 |
| 4,993,405 A | 2/1991 | Takamura et al. | |
| 5,040,069 A | 8/1991 | Matsumoto et al. | |
| 5,670,009 A * | 9/1997 | Tarn et al. .................. | 156/299 |
| 5,788,628 A * | 8/1998 | Matsuno et al. ............. | 600/127 |
| 6,030,339 A * | 2/2000 | Tatsuno et al. ............. | 600/112 |
| 6,142,930 A * | 11/2000 | Ito et al. ..................... | 600/109 |
| 6,146,326 A | 11/2000 | Pollack et al. | |
| 6,547,721 B1 * | 4/2003 | Hiroya et al. ................ | 600/133 |

FOREIGN PATENT DOCUMENTS

| | | |
|---|---|---|
| EP | 0 978 251 A1 | 2/2000 |
| JP | 9-253040 | 9/1997 |
| JP | 11-47084 | 2/1999 |
| JP | 11-231229 | 8/1999 |
| JP | 2000-60793 | 2/2000 |
| JP | 2002-301025 | 10/2002 |

* cited by examiner

*Primary Examiner*—John Leubecker
*Assistant Examiner*—Philip R Smith
(74) *Attorney, Agent, or Firm*—Scully, Scott, Murphy & Presser, P.C.

(57) ABSTRACT

The present invention provides an image pick-up device and an endoscope in which a lens member and a solid-state image pick-up device are prevented from exposure to water vapor during autoclave sterilization, and in which the diameter of an insertion portion is narrow, a rigid tip end portion is short, and assembly is performed easily. The image pick-up device of the present invention comprises an image pick-up unit for capturing an optical image obtained from incident light entering an internal cavity of a frame, and outputting an image signal of the optical image, wiring extending from the image pick-up unit in an opposite direction to the direction in which the incident light enters, this wiring being capable of transmitting the image signal, and a substrate which is disposed in the internal cavity of a frame, has holes for engaging with the wiring, one surface of which is substantially orthogonal to the axial direction of the frame, and which is formed of a member having a light-transmitting property.

20 Claims, 10 Drawing Sheets

HERMETICALLY SEALED ENDOSCOPE IMAGE PICK-UP DEVICE

This application claims benefit of Japanese Application No. 2003-060155 filed on Mar. 6, 2003, the contents of which are incorporated by this reference.

BACKGROUND OF THE INVENTION

1. Field of the Invention

The present invention relates to an image pick-up device and an endoscope, and more particularly to an image pick-up device and endoscope which are easily assembled.

2. Description of the Related Art

Conventionally in the medical field, medical endoscopes in which an insertion portion of an elongated endoscope is inserted by an operator or the like into a body cavity have been widely used to observe organs and the like inside the body and perform various curative procedures when necessary using procedural instruments inserted into an instrument channel. In the industrial field, industrial endoscopes in which the elongated insertion portion is inserted into the interior of boilers, turbines, engines, chemical plants, and soon have been widely used to observe and inspect interior damage, corrosion, and so on.

In particular, endoscopes used in the medical field in which an insertion portion is inserted into a body cavity are used to observe organs and the like and to perform various treatments or procedures using procedural instruments inserted into an instrument channel of the endoscope. Hence, when an endoscope or procedural instrument which has been used once is reused on another patient, infection from patient to patient must be prevented. For this purpose, endoscope devices must be cleaned and disinfected following an examination or medical procedure.

Disinfection and sterilization processing of endoscopes and attachments thereof such as procedural instruments is conventionally performed using a gas such as ethylene oxide gas or an antiseptic fluid. As is well known, however, sterilization gases are highly toxic, and hence complicated procedures must be carried out during the sterilization of endoscopes and their attachments in order to ensure safety. Another problem is that a large amount of time is required to perform aeration for removing gas that has bonded to an instrument following sterilization of an endoscope and its attachments. As a result, doctors, nurses, and so on are unable to use endoscopes and their attachments immediately after sterilization. Furthermore, running costs are high.

If an antiseptic fluid is used, on the other hand, a problem arises in that management of the antiseptic drug solution is complicated. Moreover, waste processing of the antiseptic fluid involves a great deal of expense.

Hence in recent years, high pressure steam sterilization known as autoclave sterilization has gradually become mainstream. Autoclave sterilization does not involve complicated operations for disinfecting and sterilizing instruments such as endoscopes (to be referred to below as "endoscopic instruments") that are subjected to sterilization, enables the immediate reuse of the endoscopic instruments following sterilization, and has low running costs. Autoclave sterilization is also known as general sterilization, and involves placing the endoscopic instrument under vacuum conditions prior to sterilization processing, using high-temperature water vapor to perform sterilization of even the minute portions of the instrument in a short amount of time, and then placing the endoscopic instrument in vacuum conditions again following sterilization processing in order to dry the instrument. According to U.S. standard ANSI/AAMIST37-1992, autoclave sterilization is defined such that during sterilization processing, an instrument is exposed for four minutes to approximately two atmospheres of pressure at 132° C.

As the diameter of the insertion portion of the endoscope decreases, the load on the patient lightens. Accordingly, the observable range within the body cavity of the patient increases, and reliable diagnoses can be made. Further, in endoscopes provided with a bending portion on the insertion portion that can be remote-controlled, the load on the patient lightens as the length of the rigid portion on the tip end side of the bending portion decreases. Accordingly, the observable range within the body cavity of the patient increases, and reliable diagnoses can be made.

A solid-state image pick-up device capable of capturing high-quality images is provided on the rigid tip end portion at the tip end of the insertion portion of the endoscope. This solid-state image pick-up device captures an image inside the body cavity and supplies a generated image signal to a monitor. The captured image is reproduced and displayed on the monitor on the basis of this image signal. Usage of this type of electronic endoscope provided with a solid-state image pick-up device has become commonplace.

The insertion portion of such an electronic endoscope, provided with a solid-state image pick-up device, has a small diameter, and various techniques are employed to reduce the length of the rigid portion at the tip end of the insertion portion.

For example, the endoscope image pick-up unit disclosed in Japanese Unexamined Patent Application Publication H11-47084 is constituted of a cover lens provided on the opening end of the rigid tip end portion, a lens frame for holding an observation optical system comprising a plurality of lenses disposed rearward of the cover lens, a device attachment frame to which the lens frame is fixed by attachment, and to which an infrared cut-off filter and a cover glass, which are disposed rearward of the observation optical system of the lens frame on the optical axis, are fixed by adhesion, a solid-state image pick-up device disposed at the rear end of the device attachment frame on the optical axis, a circuit board mounted with a drive-control circuit connected to an external lead of the solid-state image pick-up device and so on, and a signal line connection substrate for connecting the circuit board and the external lead of the solid-state image pick-up device to a signal cable.

To facilitate connection of the external lead of the solid-state image pick-up device and the circuit board in particular, and also to increase reliability, this image pick-up unit comprises a circuit board having a side through hole soldering land for soldering a center portion of the external lead of the solid-state image pick-up device, and a signal line connection substrate having a side through hole soldering land for soldering the rear end portion of the external lead. The signal line connection substrate is further provided with a through hole land for connecting the core wire and shield wire of the signal cable.

In the endoscope disclosed in Japanese Unexamined Patent Application Publication 2002-301025, the length of the rigid tip end portion of the endoscope is reduced by hermetically sealing a lens unit, a solid-state image pick-up device, a hybrid integrated circuit element (to be abbreviated to "HIC" below) for drive-controlling the solid-state image pick-up device, and so on provided on the tip end side of the insertion portion. Further, the members provided in the interior of the rigid tip end portion are constituted so as not to deteriorate as a result of autoclave sterilization.

In the endoscope disclosed in Japanese Unexamined Patent Application Publication 2000-60793, a frame in which a solid-state image pick-up device is accommodated and hermetically sealed is provided on the tip end portion. By providing a conductor on the outer surface of the frame and electrically connecting the conductor and solid-state image pick-up device while ensuring airtightness, the members provided inside the frame do not deteriorate as a result of autoclave sterilization.

SUMMARY OF THE INVENTION

An image pick-up device of the present invention comprises image pick-up means for capturing an optical image obtained from incident light entering an internal cavity of a frame, and outputting an image signal of the optical image, wiring means extending from the image pick-up means in an opposite direction to the direction in which the incident light enters, which are capable of transmitting the image signal, and a substrate which is disposed in the internal cavity, has engaging portions for engaging with the wiring means, one surface of which is substantially orthogonal to the axial direction of the frame, and which is formed of a member having a light-transmitting property.

DETAILED DESCRIPTION OF THE PREFERRED EMBODIMENTS

A first embodiment of the present invention will be described in detail below with reference to the drawings.

Figure 1:
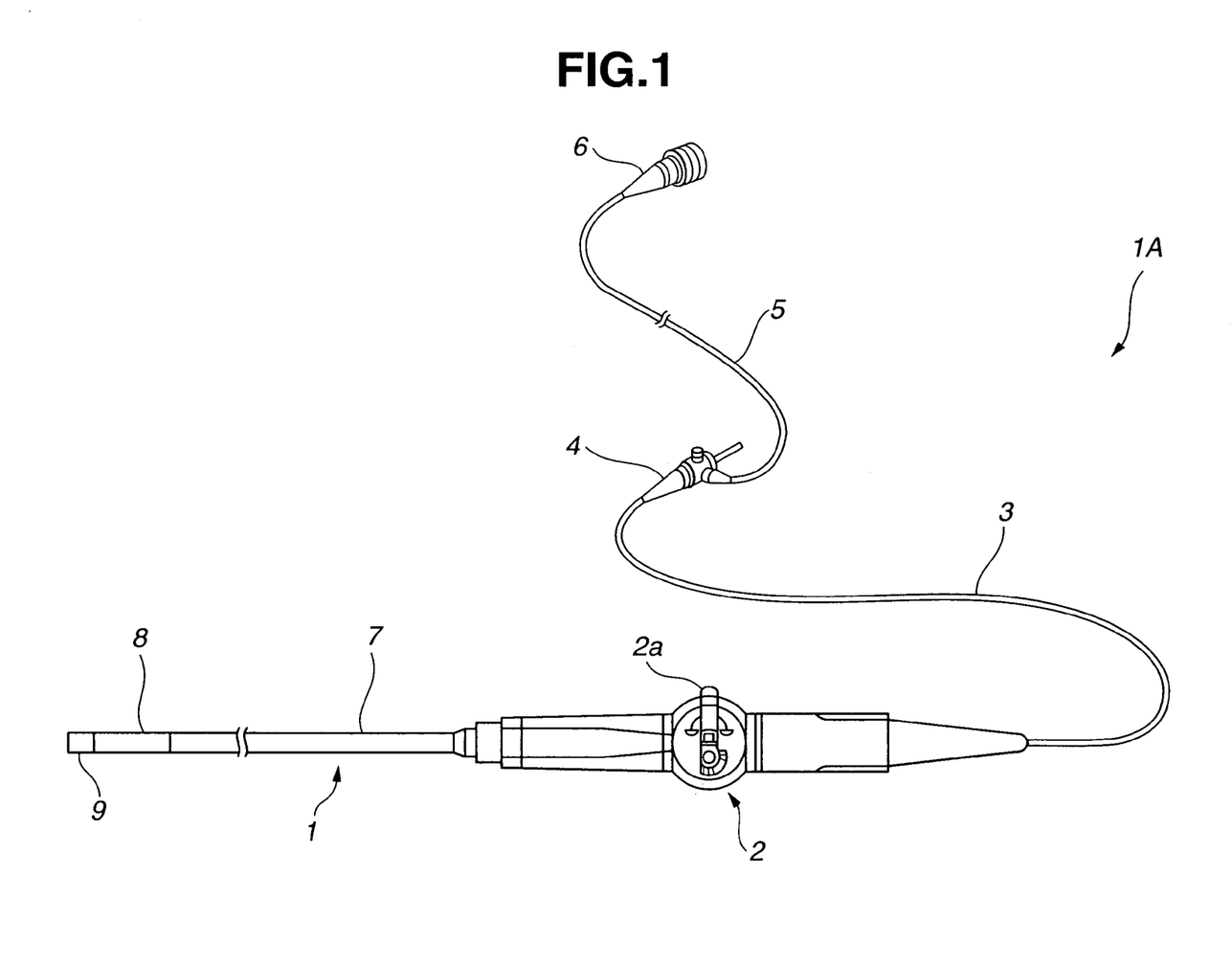
FIG. 1 is an illustrative diagram showing the constitution of an endoscope using an image pick-up device according to a first embodiment of the present invention.
Figure 2:
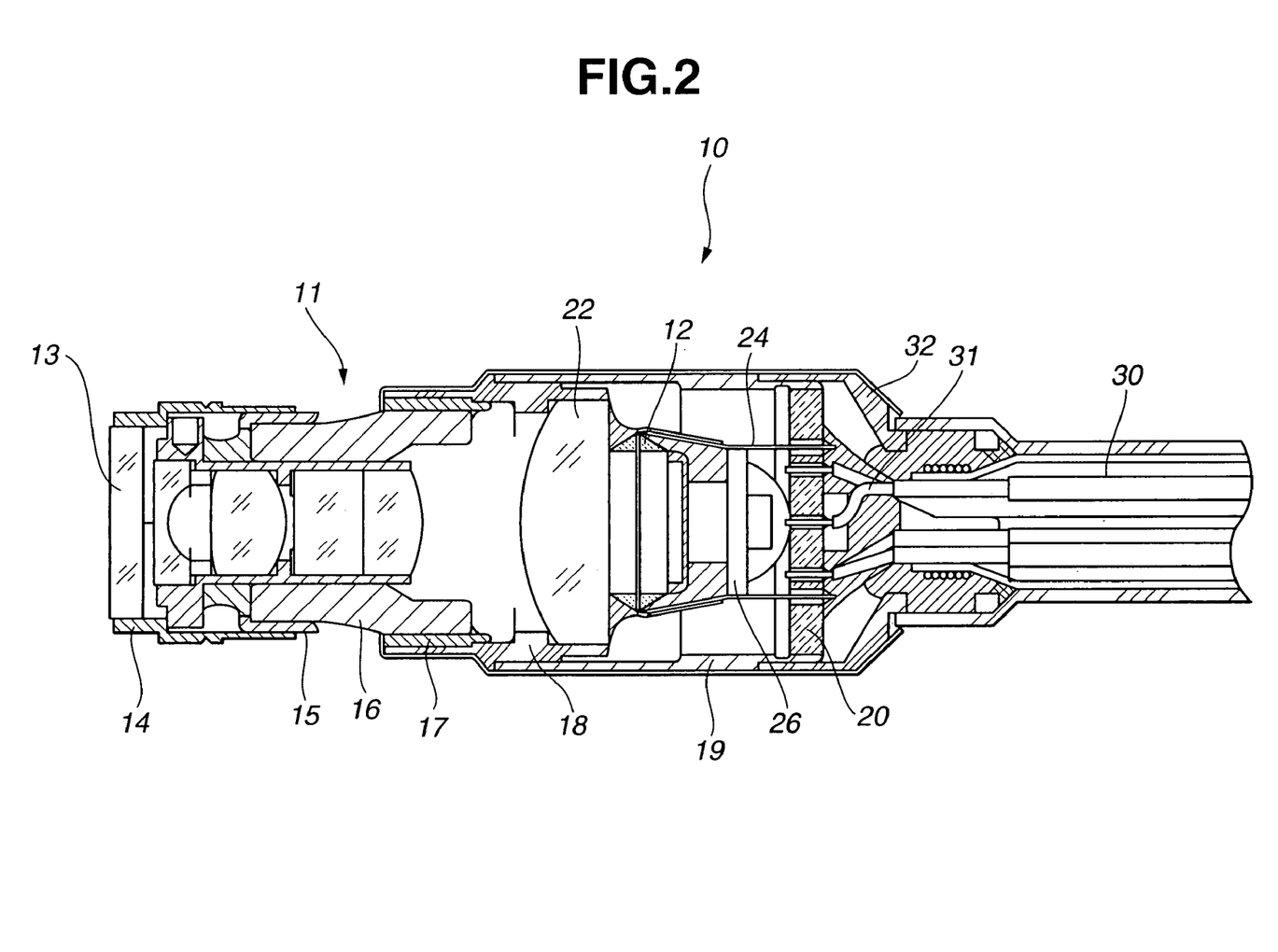
FIG. 2 is a sectional view showing the constitution of the image pick-up device according to the first embodiment of the present invention.
Figure 3:
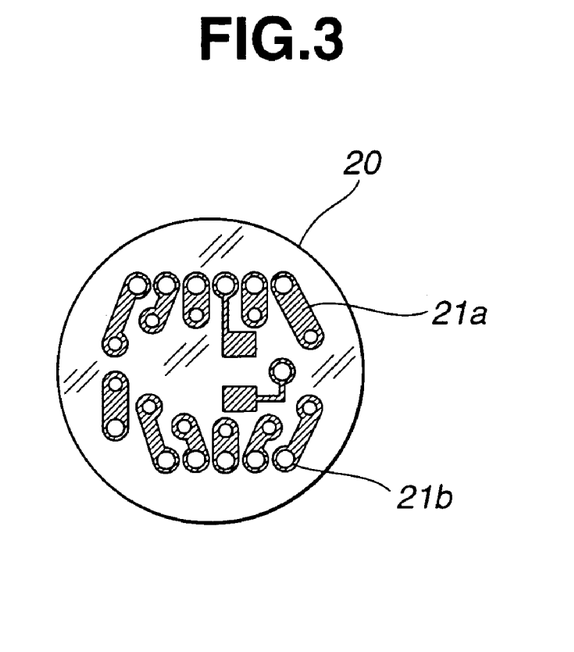
FIG. 3 is a plan view showing the constitution of a transparent substrate used in the image pick-up device according to the first embodiment of the present invention.
Figure 4:
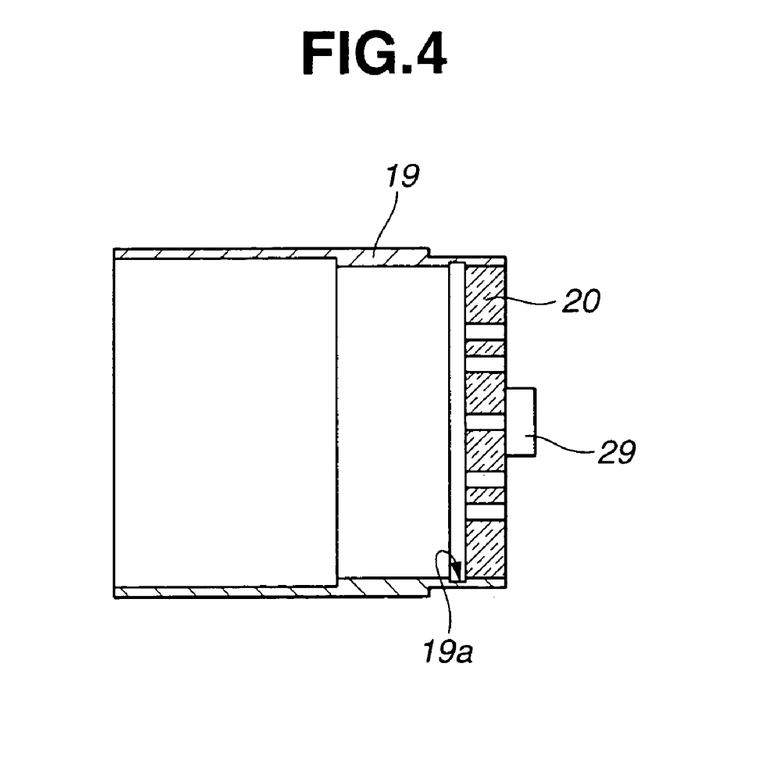
FIG. 4 is a sectional view showing a condition in which the transparent substrate is mounted in a substrate frame of the image pick-up device according to the first embodiment of the present invention.
Figure 5:
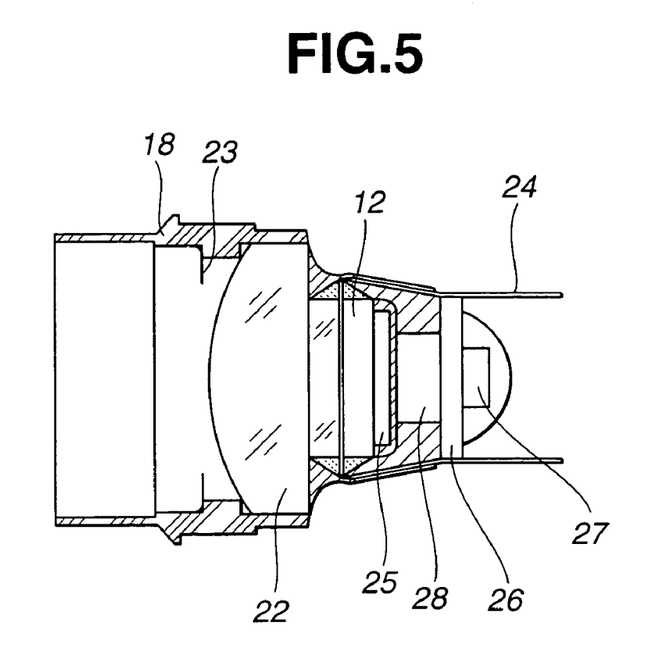
FIG. 5 is a sectional view showing a condition in which a lens holder and a solid-state image pick-up device are mounted in the image pick-up device according to the first embodiment of the present invention.
Figure 6:
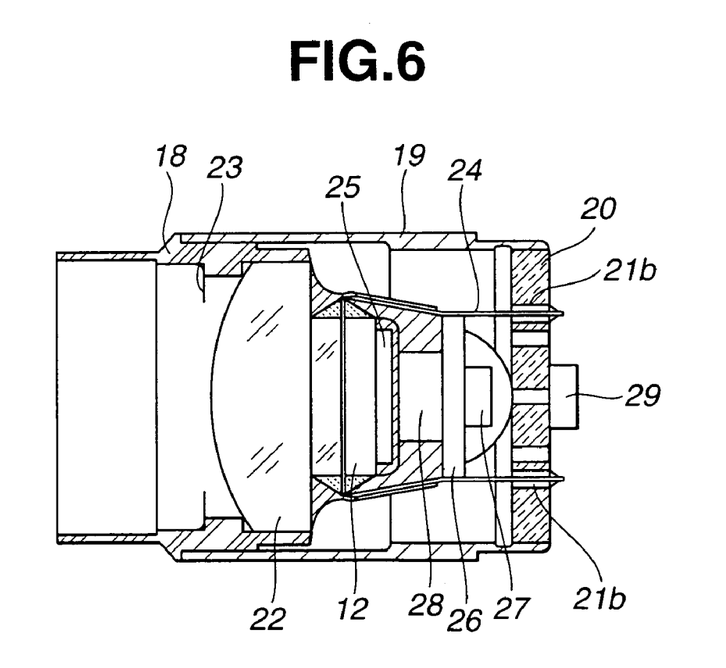
FIG. 6 is a sectional view showing a condition in which the lens holder and solid-state image pick-up device of FIG. 5 are mounted in the substrate frame of FIG. 4 in the image pick-up device according to the first embodiment of the present invention.
Figure 7:
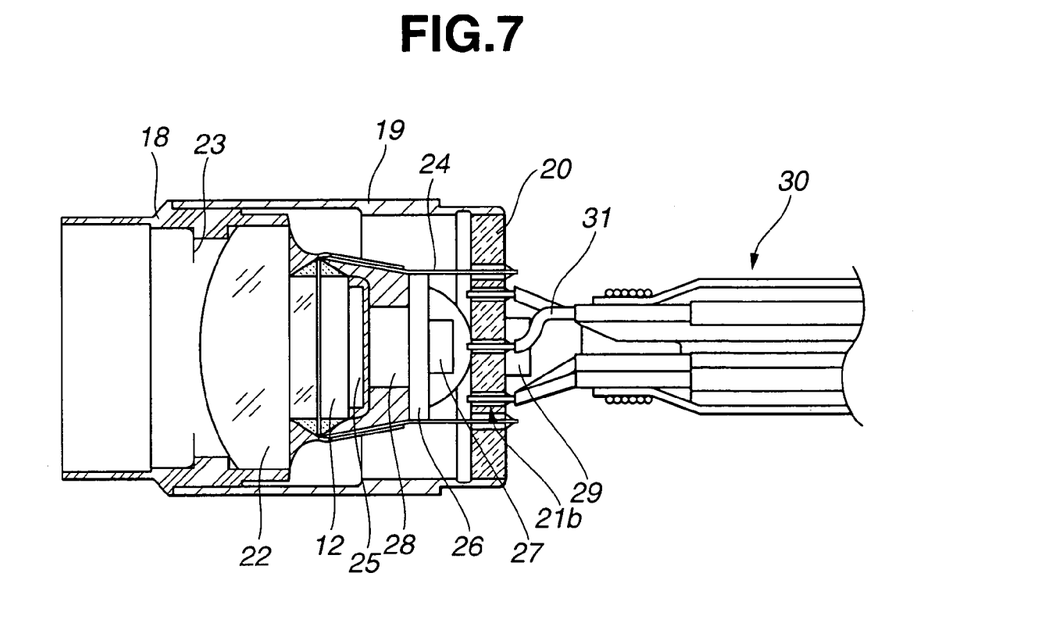
FIG. 7 is a sectional view showing a condition in which a cable is connected to the substrate frame mounted with the lens holder and solid-state image pick-up device of FIG. 6 in the image pick-up device according to the first embodiment of the present invention.
Figure 8:
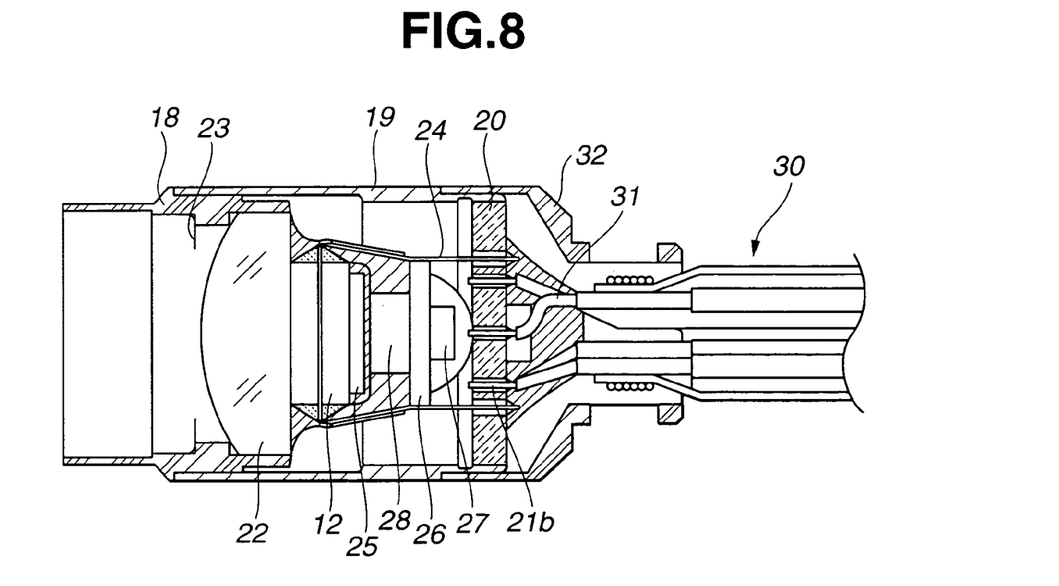
FIG. 8 is a sectional view showing a condition in which a cable holder is attached to the substrate frame connected to the cable in FIG. 7 in the image pick-up device according to the first embodiment of the present invention.

FIG. 1 is an illustrative diagram showing the constitution of an endoscope using an image pick-up device according to the first embodiment of the present invention. FIG. 2 is a sectional view showing the constitution of the image pick-up device according to the first embodiment of the present invention. FIG. 3 is a plan view showing the constitution of a transparent substrate used in the image pick-up device according to the first embodiment of the present invention. FIGS. 4 through 8 are sectional views illustrating assembly procedures of the image pick-up device according to the first embodiment of the present invention. FIG. 4 is a sectional view showing a condition according to the first embodiment of the present invention in which the transparent substrate is mounted in a substrate frame. FIG. 5 is a sectional view showing a condition according to the first embodiment of the present invention in which a lens holder and a solid-state image pick-up device are mounted in the image pick-up device. FIG. 6 is a sectional view showing a condition in which the lens holder and solid-state image pick-up device of FIG. 5 are mounted in the substrate frame of FIG. 4. FIG. 7 is a sectional view showing a condition in which a cable is connected to the substrate frame mounted with the lens holder and solid-state image pick-up device of FIG. 6. FIG. 8 is a sectional view showing a condition in which a cable holder is attached to the substrate frame connected to the cable in FIG. 7.

First, an endoscope using an image pick-up device according to the first embodiment of the present invention will be described using FIG. 1. This endoscope 1A is constituted of a flexible elongated insertion portion 1 which is inserted into the body, an operating portion 2 provided on the base end portion of the insertion portion 1, a universal cord 3 which extends from the operating portion 2, a light guide connector 4 provided on the end portion of the universal cord 3 and connected to a light source device, not shown in the drawing, of the endoscope device, a camera cable 5 which bifurcates from the light guide connector 4, and a camera connector 6 provided on the end portion of the camera cable 5 and connected to a camera control unit, not shown in the drawing, of the endoscope device.

In succession from the operating portion 2 side, the insertion portion 1 is constituted of a bendable tube portion 7 formed of an elastic material, a bending portion 8 in which a plurality of bending parts are connected, and which is caused to bend upward, downward, left, and right, for example, by operating a bending operation knob 2a provided on the operating portion 2, and a rigid tip end portion 9 formed of a rigid member.

The rigid tip end portion 9 has two or more frames. Each frame has the outer surface and the inner surface. In this embodiment, each frame is substantially tubular shape. Therefore, as for each frame, internal cavity is defined by the inner surface.

The operating portion 2 is provided with the bending knob 2a for causing the bending portion 8 of the insertion portion 1 to bend, and a procedural instrument insertion hole, an air supply and intake hole, and a water supply and intake port, not shown in the drawing, which communicate respectively with a procedural instrument channel, an air supply and intake channel, and a water supply and intake channel provided from the operating portion 2 to the insertion portion 1.

The universal cord 3 is installed with a light guide which is connected to the light guide connector 4 so as to guide illumination light from the light source device of the endoscope device, and the camera cable 5. The light guide and camera cable 5 are laid from the operating portion 2 to the rigid tip end portion 9 of the insertion portion 1.

The illumination light that is projected to the light guide connector 4 from the light source device of the endoscope device is guided by the light guide so as to be projected onto the observation site from the rigid tip end portion 9 of the insertion portion 1.

The camera cable 5 is used for transmitting drive-control signals for drive-controlling the solid-state image pick-up device of an image pick-up unit 10 to be described below which is provided on the rigid tip end portion 9 of the insertion portion 1, and captured image signals which are captured and generated by the solid-state image pick-up device, to and from the camera control unit of the endoscope device which is connected to the camera connector 6.

More specifically, the observation site is illuminated by the illumination light projected thereon from the rigid tip end portion 9 of the insertion portion 1, and an image thereof is captured by the solid-state image pick-up device. An image signal of the captured image is then subjected to predetermined signal processing by the camera control unit of the endoscope device to generate a standard video signal. On the basis of this video signal, a monitor, not shown in the drawing, of the endoscope device reproduces and displays the captured image. A doctor or the like is able to observe and examine the observation site by means of the captured image that is reproduced and displayed on the monitor of the endoscope device.

Next, the image pick-up unit 10 provided in the interior of the rigid tip end portion 9 of the insertion portion 1 and serving as the image pick-up device according to the first embodiment of the present invention will be described using FIG. 2.

The image pick-up unit 10 basically comprises a lens unit 11 in which a plurality of optical lenses are disposed and a solid-state image pick-up device 12 having an imaging surface on which images of the observation site, having passed through the lens unit 11, are formed.

In the lens unit 11, a plurality of optical lenses are fixed inside a substantially tubular lens frame, and a front end lens 13 which constitutes the forefront portion of the lens unit 11 is disposed on the incidence side of the observation site image.

The front end lens 13 is formed of a material having a high tolerance to water vapor, for example sapphire glass or silica glass. Metallization processing is performed on the outer peripheral surface of the front end lens 13. Having been subjected to metallization processing, the front end lens 13 is joined to the front end inner peripheral surface of a tubular device frame 14 by brazing or soldering. Note that to enable brazing or soldering using nickel, gold, or the like, a coating is applied to the surface of the inner periphery of the device frame 14 at the site where the front end lens 13 is to be brazed or soldered.

In other words, the outer peripheral surface of the front end lens 13 and the inner peripheral surface of the device frame 14 are joined by soldering, and the joint surface is hermetically sealed such that air does not infiltrate therein.

A lens frame 11a in which the plurality of optical lenses constituting the lens unit 11 are disposed is provided in the interior of the device frame 14 to which the front end lens 13 is hermetically joined.

More specifically, the device frame 14 and a ceramic frame 16 are joined via a first pipe 15, and the lens unit 11 is provided in the interior of the device frame 14 and ceramic frame 16.

The outer peripheral surface of the tubular first pipe 15 is joined to the inner peripheral surface of the rear end side of the device frame 14. The outer peripheral surface of the front end side of the tubular ceramic frame 16, which is formed of a dense ceramic such as alumina, is joined to the inner peripheral surface of the rear end side of the first pipe 15.

The inner peripheral surface of a tubular second pipe 17 is joined to the outer peripheral surface of the rear end side of the ceramic frame 16. A tubular lens holder 18 is joined to the outer peripheral surface of the second pipe 17. The inner peripheral surface of a tubular substrate frame 19 is joined to the outer peripheral surface of the lens holder 18. Note that a lens 22 which constitutes the rearmost portion of the lens unit 11 is joined and fixed to the inner peripheral surface of the rear end side of the lens holder 18.

The device frame 14 and first pipe 15, the first pipe 15 and ceramic frame 16, the ceramic frame 16 and second pipe 17, the second pipe 17 and lens holder 18, and the lens holder 18 and substrate frame 19 are respectively joined by a joining method such as laser welding, brazing or soldering, or joining using a metal, for example fusion welding or pressure welding, and are sealed hermetically such that air does not infiltrate the joint surface.

Note that the device frame 14, first pipe 15, second pipe 17, lens holder 18, and substrate frame 19 are formed of a material with a high tolerance to water vapor such as stainless steel, for example.

The joining site on the ceramic frame 16 is subjected to surface processing by means of Mo—Mn baking in an active metal soldering method, plating, PVD, or similar, thus enabling airtight joining of the first pipe 15 and second pipe 17.

A transparent substrate 20 formed of a transparent material is adhered to the inner peripheral surface of the rear end of the substrate frame 19. The transparent substrate 20 is formed of a material having a high tolerance to water vapor and comparatively good mechanical strength, such as sapphire glass, Pyrex®, or silica glass, for example.

The outer peripheral surface of the transparent substrate 20 is subjected to metallization processing, and having been subjected to metallization processing, the outer peripheral surface is joined to the inner peripheral surface of the substrate frame 19 by brazing or soldering. Note that to enable brazing or soldering using nickel, gold, or the like, a plating coating or the like is applied to the inner peripheral surface of the substrate frame 19 at the site where the transparent substrate 20 is to be soldered. Hence the outer peripheral surface of the transparent substrate 20 and the inner peripheral surface of the substrate frame 19 are hermetically joined, and air is prevented from infiltrating the joint surface.

As shown in FIG. 3, the overall shape of the transparent substrate 20 is disc-form, and a plurality of through holes 21b are drilled from the front face to the back face. A plurality of patterns enabling wire soldering are provided on the front face of the transparent substrate 20 on the opening side of the substrate frame 19 around the respective perimeters of the through holes 21b. Further, the plurality of patterned portions 21a enabling wire soldering are formed on the front face of the transparent substrate 20 so as to connect related through holes 21b to each other.

More specifically, the through holes 21b serve as engaging portions into which lead wires or the like serving as connection portions and formed of conductors are inserted. By soldering the pin-form lead wires or the like to the patterned portions 21a around the through holes 21b, the pin-form lead wires or the like and the patterned portions 21a are electrically connected. Further, since the transparent substrate 20 is formed of a transparent member, the positions of the pin-form lead wires or the like can be confirmed easily when the pin-form lead wires or the like are inserted into the through holes 21b. Thus a worker manufacturing the image pick-up unit 10 is able to recognize the positional relationships between the pin-form lead wires or the like and the through holes 21b easily.

Lead wires 24 serving as connection portions to the solid-state image pick-up device 12, or signal lines 31 of a cable 30 to be described below, are inserted into the through holes 21b serving as engaging portions of the transparent substrate 20, and connected thereto by soldering.

When the lead wires 24 of the solid-state image pick-up device 12 and the signal lines 31 of the cable 30 are connected to the transparent substrate 20 by soldering, a cable holder 32 is joined to the outer peripheral surface of the substrate frame 19, and processing to fold and latch the cables and so on is performed.

The solid-state image pick-up device 12 and a substrate 26 mounted with various electronic components are disposed on the optical axis at the rear end side of the lens 22 which is joined to the lens holder 18.

Next, the assembly procedure for the image pick-up unit 10 constituted in this manner will be described using FIGS. 4 through 8.

First, as shown in FIG. 4, an assembly worker (to be referred to as "worker" below) mounts the transparent substrate 20 onto the rear end inner peripheral surface of the substrate frame 19 and solders the two components together. When mounting the transparent substrate 20, the worker ensures that the face which is formed with the patterned portions 21a is positioned facing the outside of the rear end side of the substrate frame 19. A groove portion 19a for restricting the flow of molten brazing filler metal or solder during soldering of the transparent substrate 20 is provided on the inside of the substrate frame 19 to which the transparent substrate 20 is to be soldered. The plating and coating applied to facilitate soldering of the transparent substrate 20 to the rear end inner peripheral surface of the substrate frame 19 are removed from this groove portion 19a.

When the transparent substrate 20 is soldered hermetically to the substrate frame 19, the worker connects an electronic component 29, such as a condenser and resistor, which constitutes an electronic circuit required for drive-control of the solid-state image pick-up device 12 and read-out control of image-capture signals from the solid-state image pick-up device, to the patterned portions 21a formed on the front face of the transparent substrate 20 by soldering.

Note that when soldering the substrate frame 19 and transparent substrate 20, soldering may be performed with the entirety of the soldered body at a high temperature, and a vacuum chamber or a comparatively high temperature brazing filler metal (hard solder) such as hydrogen furnace solder may be used. The worker may also use flux to perform cleaning following the soldering. Note that in this case, the worker must attach the electronic component 29 after the soldering.

Next, mounting of the solid-state image pick-up device into the lens holder 18 will be described using FIG. 5.

The solid-state image pick-up device 12 is positioned on the optical axis of the lens 22, which is fitted into and thereby joined to the lens holder 18, and then joined to the lens 22 by an optical adhesive. A light-shielding mask 23 for restricting the range of the object image entering the lens 22 is fixed to the inner periphery of the lens holder 18 by adhesion. The light of the object image within the restricted range of the light-shielding mask 23 passes through the lens 22 and is formed as an image on the imaging surface of the solid-state image pick-up device 12. Note that here, a protective glass is fixed between the lens 22 and the imaging surface of the solid-state image pick-up device 12.

A plurality of lead wires 24 extend from the solid-state image pick-up device 12. The lead wires 24 are bent by the side faces of the solid-state image pick-up device 12 and then extend rearward from the side face of the solid-state image pick-up device 12. The bent portions are reinforced by an adhesive.

An insulating member 25 for applying electrical insulation is bonded to the back face of the solid-state image pick-up device 12 by an adhesive having an insulating property. The substrate 26 is disposed on either side of the insulating member 25 so as to electrically connect the intermediate portions of the lead wires 24 of the solid-state image pick-up device 12.

A pattern land for connecting the lead wires 24 of the solid-state image pick-up device 12 is provided on the outer surface of the substrate 26. A hybrid IC (to be abbreviated to "HIC" below) 27 for performing drive-control of the solid-state image pick-up device 12 and read-out control of image-capture signals is mounted on the opposite surface of the substrate 26 to the solid-state image pick-up device 12. An electronic component 28 such as a condenser and resistor is mounted on the surface of the substrate 26 on the side of the solid-state image pick-up device 12. The HIC 27 and electronic component 28 are connected to the lead wires 24 of the solid-state image pick-up device 12 via the aforementioned pattern land provided on the outer surface of the substrate 26.

Thus the solid-state image pick-up device 12 is joined to the back face of the lens 22 in the lens holder 18, and the intermediate portions of the lead wires 24 of the solid-state image pick-up device 12 are electrically connected to the substrate 26 mounted with the HIC 27 and electronic component 28. Next, the periphery of the solid-state image pick-up device 12, the bent portion of the lead wires 24, the periphery of the insulating member 25, and the periphery of the electronic component 28, all of which are disposed between the lens 22 and the substrate 26, are filled with an insulating adhesive in order to reinforce the mechanical strength thereof.

A procedure for mounting the lens holder 18 incorporated with the solid-state image pick-up device 12 and substrate 26, as described above, into the substrate frame 19 incorporated with the transparent substrate 20, as described in FIG. 4, will now be described using FIG. 6.

The worker fits the substrate frame 19 incorporated with the transparent substrate 20 onto the outer peripheral surface of the lens holder 18 incorporated with the solid-state image pick-up device 12 and substrate 26. At this time, the worker fits the substrate frame 19 onto the outer peripheral surface of the lens holder 18 while inserting the lead wires 24 of the solid-state image pick-up device 12 into the predetermined through holes 21b formed in the transparent substrate 20.

Conventionally, the lead wires 24 of the solid-state image pick-up device 12 are flexible, and hence position alignment to insert the leadwires 24 into the throughholes 21b is difficult. In the position alignment of the through holes 21b and lead wires 24 according to this embodiment, however, the transparent substrate 20 is transparent, and hence the position of the pin-form leadwires 24 is confirmed visually by the worker through the transparent substrate 20. Hence the worker may fit the substrate frame 19 onto the outer peripheral surface of the lens holder 18 while inserting the lead wires 24 into the through holes 21b with comparative ease. Soldering is performed to electrically connect the lead wires 24 inserted into the through holes 21b and the patterned portions 21a on the periphery of the through holes 21b into which the lead wires 24 are inserted. Through this soldering, the lead wires 24, through holes 21b, and patterned portions 21a are joined so as to secure airtightness.

Once the lead wires 24 of the solid-state image pick-up device 12 have been inserted into and soldered to the predetermined through holes 21b of the transparent substrate 20 in this manner, the fitted portion between the substrate frame 19 and lens holder 18 is joined hermetically by laser welding or the like. Once the lens holder 18 and substrate frame 19 have been joined hermetically, the plurality of signal lines 31 of the cable 30 are inserted into the predetermined through holes 21b of the transparent substrate 20 in the substrate frame 19 and soldered as shown in FIG. 7. The signal lines 31 of the cable 30 are inserted into the through holes 21b from the outer surface of the transparent substrate 20. The signal lines 31 are then soldered to the patterned portions 21a on the periphery of the through holes 21b such that the through holes 21b and the signal lines 31 of the cable 30 are hermetically joined.

The space portion formed by the lens holder 18 and substrate frame 19, or in other words the solid-state image pick-up device 12, the substrate 26, and the face of the transparent substrate 20 on the side of the solid-state image pick-up device 12, is thus made airtight such that outside air does not infiltrate. Note that the other end of the cable 30 is connected to the aforementioned camera connector 6, and thus various signals are transmitted and received between the solid-state image pick-up device 12 and the camera control unit that is connected to the camera connector 6.

Once the cable 30 has been hermetically joined to the transparent substrate 20, the cable holder 32 is joined and fixed to the outer peripheral surface of the substrate frame 19 as shown in FIG. 8.

When the cable holder 32 is to be joined and fixed to the substrate frame 19, the worker inserts the cable 30 into the tubular cable holder 32 in advance. With the cable 30 inserted into the cable holder 32, insertion of the signal lines 31 into the through holes 21b of the transparent substrate 20 and connection thereof by soldering is performed as described in FIG. 7. Once the signal lines 31 have been connected by soldering, the worker applies an adhesive to the signal lines 31 and the end portion of the cable 30 in order to reinforce the mechanical strength of the end portion of the cable 30. Following this strength reinforcement using adhesive, the inner peripheral surface of the cable holder 32 inserted in advance with the cable 30 is fitted into and thus joined to the outer peripheral surface of the substrate frame 19.

Thus the substrate frame 19 is hermetically joined to the lens holder 18 provided with the solid-state image pick-up device 12 and the substrate 26 on which the HIC 27 and electronic component 28 are mounted. Once the lead wires 24 of the solid-state image pick-up device 12 and the signal lines 31 of the cable 30 have been respectively connected hermetically to the transparent substrate 20 of the substrate frame 19, the lens unit 11 comprised in the device frame 14, first pipe 15, and ceramic frame 16 is hermetically joined to the inside front end of the lens holder 18 via the second pipe 17, and thus the image pick-up unit 10 is assembled.

Note that the outer peripheral surface of the second pipe 17, lens holder 18, substrate frame 19, and cable holder 32 are covered with an insulating protective tube.

As described above, the transparent substrate 20 is used as the substrate that is inserted from both sides with and connected to the plurality of flexible leadwires 24, which extend from the solid-state image pick-up device 12 with a narrow space therebetween, and the plurality of comparatively narrow signal lines 31 of the cable 30, and hence when inserting the lead wires 24 and signal lines 31 into the through holes 21b, the worker can confirm the position of the lead wires 24 and so on visually from one side. Accordingly, soldering of the inserted wires to the substrate improves in efficiency, and the shape of the substrate and mounting space can be minimized. As a result, the outer diameter of the insertion portion 1 can be reduced and the rigid length in the axial direction of the rigid tip end portion 9 of the insertion portion 1 can also be reduced.

By maintaining the interior space surrounded by the front end lens 13, device frame 14, first pipe 15, ceramic frame 16, second pipe 17, lens holder 18, substrate frame 19, and transparent substrate 20 in an airtight condition, the infiltration of water vapor into the interior space during autoclave sterilization and the like can be securely prevented.

Hence, the lens unit 11 disposed in the interior space of the image pick-up device does not suffer lens clouding caused by the infiltration of water vapor, and the interior components such as the lens unit 11, solid-state image pick-up device 12, and so on installed in the interior space are not exposed to water vapor. As a result, the interior components provided in the interior of the image pick-up device are not caused to degenerate due to water vapor.

Further, through the transparent substrate 20, the worker can visually check the condition of the solid-state image pick-up device 12, HIC 27, electronic component 28, and soon and confirm that no water vapor has infiltrated the airtight space in which these components are disposed prior to attachment of the cable holder 32 to the substrate frame 19, or by removing the cable holder 32 from the substrate frame 19 prior to the joining of the cable holder 32 to the substrate frame 19.

Figure 9:
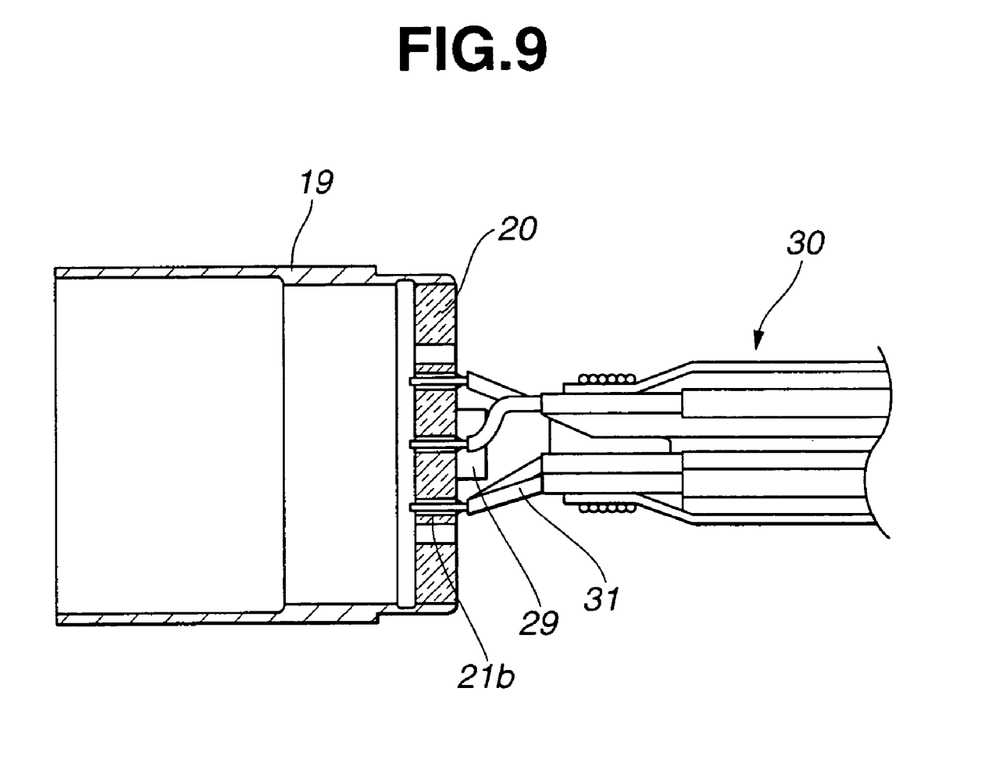
FIG. 9 is a sectional view showing a condition in which a cable is connected to the transparent substrate of the substrate frame in a modified example of the image pick-up device according to the first embodiment of the present invention.

Next, a modified example of the first embodiment will be described using FIG. 9. In the first embodiment described above, a case in which the transparent substrate 20 is mounted in the substrate frame 19 and the electronic component 29 is attached to the transparent substrate 20, as shown in FIG. 4, was described. In the modified example of the first embodiment, on the other hand, as shown in FIG. 9, the electronic component 29 is attached to the transparent substrate 20, the signal lines 31 of the cable 30 are inserted into predetermined through holes 21b in the transparent substrate 20, and the patterned portions 21a around the through holes 21b inserted with the signal lines 31 are connected by soldering. The worker then joins the transparent substrate 20, to which the electronic component 29 and the signal lines 31 of the cable 30 are connected, to the inner peripheral surface of the substrate frame 19 so as to be airtight.

The lead wires 24 of the solid-state image pick-up device 12 maybe inserted into the through holes 21b in the transparent substrate 20 and then soldered thereto so as to connect the lead wires 24 and through holes 21b while the transparent substrate 20, to which the electronic component 29 and the signal lines 31 of the cable 30 are connected, is joined hermetically to the substrate frame 19 and, as shown in FIG. 7, the lens holder 18 incorporated with the solid-state image pick-up device 12 and substrate 26 is joined to the substrate frame 19.

As a result, the soldering operation of the cable 30 and transparent substrate 20 is made easier, and since the cable 30 is already soldered to the transparent substrate 20 during soldering of the transparent substrate 20 and solid-state image pick-up device 12, the danger of electrostatic breakdown of the solid-state image pick-up device 12 during connection by soldering of the lead wires 24 of the solid-state image pick-up device 12 and the cable 30 to the transparent substrate 20 is reduced.

Figure 10:
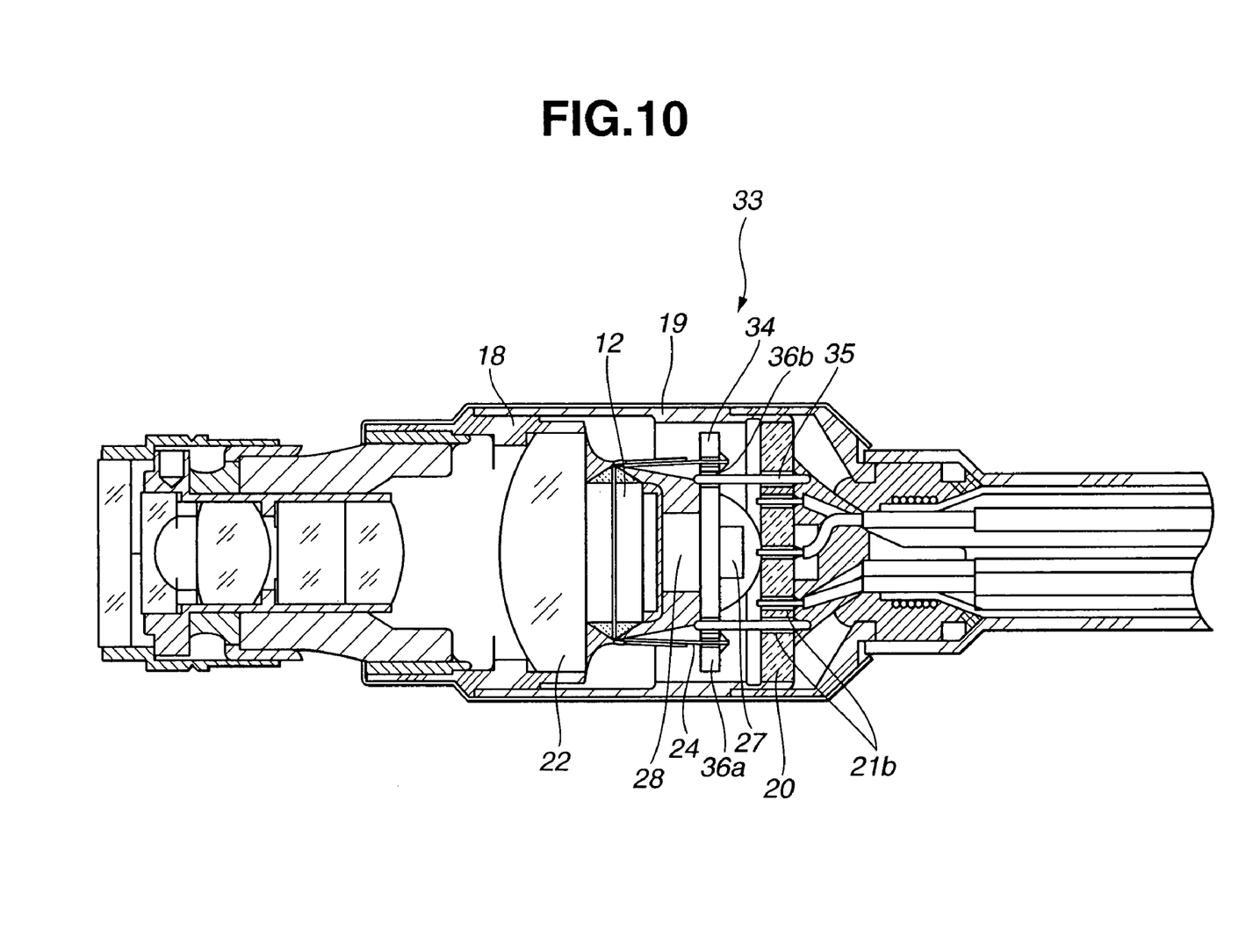
FIG. 10 is a sectional view showing the constitution of an image pick-up device according to a second embodiment of the present invention.

Next, an image pick-up device according to a second embodiment of the present invention will be described using FIG. 10. FIG. 10 is a sectional view showing the constitution of the image pick-up device according to the second embodiment of the present invention. Note that identical parts to those in FIGS. 1 through 9 have been allocated identical reference symbols, and detailed description thereof will be omitted.

In an image pick-up unit 33 of the image pick-up device of the second embodiment, the solid-state image pick-up device 12 is disposed on the rear face of the lens 22 of the lens holder 18. Further, a second transparent substrate 34 pre-installed with the HIC 27 and electronic component 28 is disposed on the rear face of the solid-state image pick-up device 12.

The second transparent substrate 34 is provided with through holes 36a for attaching, soldering, and connecting the lead wires 24 of the solid-state image pick-up device 12, and through holes 36b into which solderable current-carrying pins 35 are inserted.

The second transparent substrate 34 is formed of a transparent member formed of sapphire, white board, a glass material, or similar.

The lead wires 24 of the solid-state image pick-up device 12 are inserted into the through holes 36a of the second transparent substrate 34. The through holes 36a and lead wires 24 are then electrically connected on the opposite face of the second transparent substrate 34 on which the solid-state image pick-up device 12 is positioned by soldering.

One end of the current-carrying pins 35 is inserted into the through holes 36b of the second transparent substrate 34, whereupon the through holes 36b and current-carrying pins 35 are electrically connected by soldering. The other end of the current-carrying pins 35 is inserted into the predetermined through holes 21b of the transparent substrate 20, whereupon the through holes 21b and current-carrying pins 35 are electrically connected by soldering.

Hence the current-carrying pins 35 are electrically connected to the second transparent substrate 34, and to the transparent substrate 20 which is hermetically joined to the substrate frame 19 and to which the core wires 31 of the cable 30 are connected.

Note that the current-carrying pins 35 are at least connected hermetically to the through holes 21b of the transparent substrate 20 by soldering. In so doing, the space constituted by the lens holder 18 and substrate frame 19 is maintained in an airtight condition similarly to the first embodiment.

When the second transparent substrate 34 is used, it becomes easier for the worker to insert the flexible lead wires 24 of the solid-state image pick-up device 12 into the through holes 36a of the second transparent substrate 34. Further, since the current-carrying pins 35 are connected to the second transparent substrate 34 by soldering, the worker can easily solder and thus connect the current-carrying pins 35 to the transparent substrate 20.

The image pick-up device of the second embodiment possesses the same advantages and effects as the first embodiment described above, and since positioning of the respective constitutions is performed during soldering of the current-carrying pins 35 of the second transparent substrate 34 to the transparent substrate 20, an improvement in assembly work efficiency is achieved. Furthermore, the worker is able to observe the condition of the solid-state image pick-up device 12, HIC 27, and electronic component 28 through the transparent substrate 20 and second transparent substrate 34, and hence can determine whether water vapor has infiltrated the airtight space in which these components are disposed, and so on.

Figure 11:
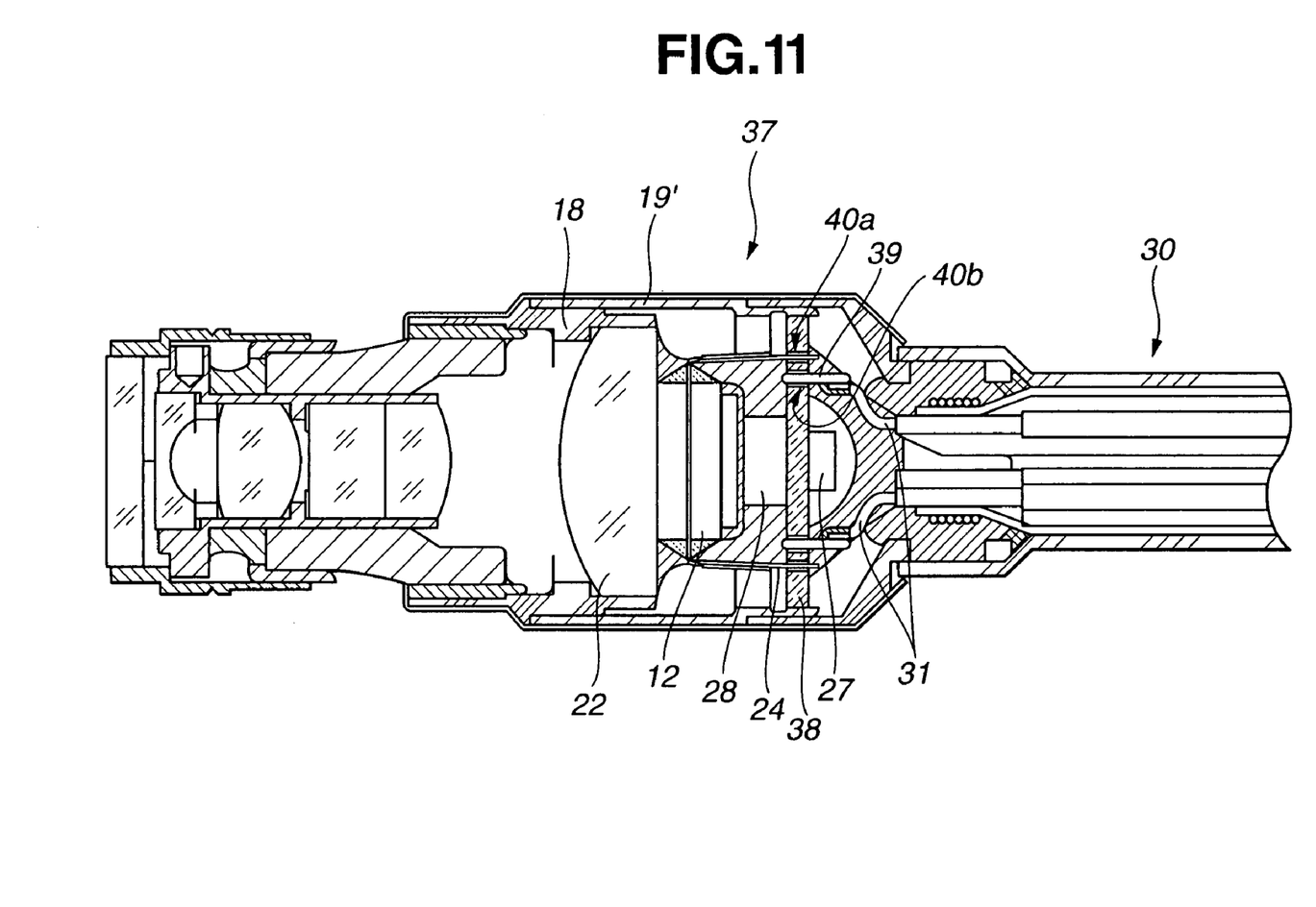
FIG. 11 is a sectional view showing the constitution of an image pick-up device according to a third embodiment of the present invention.

Next, an image pick-up device according to a third embodiment of the present invention will be described using FIG. 11. FIG. 11 is a sectional view showing the constitution of the image pick-up device according to the third embodiment of the present invention. Note that identical parts to those in FIGS. 1 through 9 have been allocated identical reference symbols, and detailed description thereof will be omitted.

In an image pick-up unit 37 of the image pick-up device of the third embodiment, the solid-state image pick-up device 12 is disposed on the rear face of the lens 22 of the lens holder 18, and a transparent substrate 38 pre-installed with the HIC 27 and electronic component 28 is disposed on the rear face of the solid-state image pick-up device.

The transparent substrate 38 is provided with through holes 40a into which the lead wires 24 of the solid-state image pick-up device 12 are inserted and then connected by soldering, and through holes 40b into which solderable terminal pins 39 are inserted.

The transparent substrate 38 is formed of a similar transparent member to the transparent substrate 20 and second transparent substrate 34 described above.

The lead wires 24 of the solid-state image pick-up device 12 are inserted into the through holes 40a of the transparent substrate 38. The through holes 40a and lead wires 24 are then electrically connected by soldering which is performed on the opposite face of the transparent substrate 38 on which the solid-state image pick-up device 12 is positioned.

One end of the terminal pins 39 is inserted into the through holes 40b of the transparent substrate 38 and then connected thereto by soldering. The core wires 31 of the cable 30 are wrapped around the other end of the terminal pins 39 and then connected thereto by soldering.

When the transparent substrate 38 is used, it becomes easier to insert the flexible lead wires 24 of the solid-state image pick-up device 12 into the through holes 40a of the transparent substrate 38. Further, the worker can connect the terminal pins 39 to the transparent substrate 38 by soldering performed in advance when hermetically joining the substrate frame 19' to the lens holder 18. Thus the worker is able to seal the space constituted by the lens holder 18 and substrate frame 19' in an airtight condition prior to connection of the cable 30.

By establishing the airtight space before attaching the cable 30 to the terminal pins 39 in this manner, the air tightness can be inspected using a bombing method of an He Leak Detector or the like, and hence a precise inspection is possible. (When the cable 30 is connected, He leaks into the interior of the cable 30 and is adsorbed. This He is then mistakenly detected by the He Leak Detector. As a result, it becomes difficult for the worker to determine whether or not the joint portion of the lens holder 18 and substrate frame 19' is leaking.)

Further, it becomes easier for the worker to connect the terminal pins 39 and signal lines 31 of the cable 30 by soldering.

Figure 12:
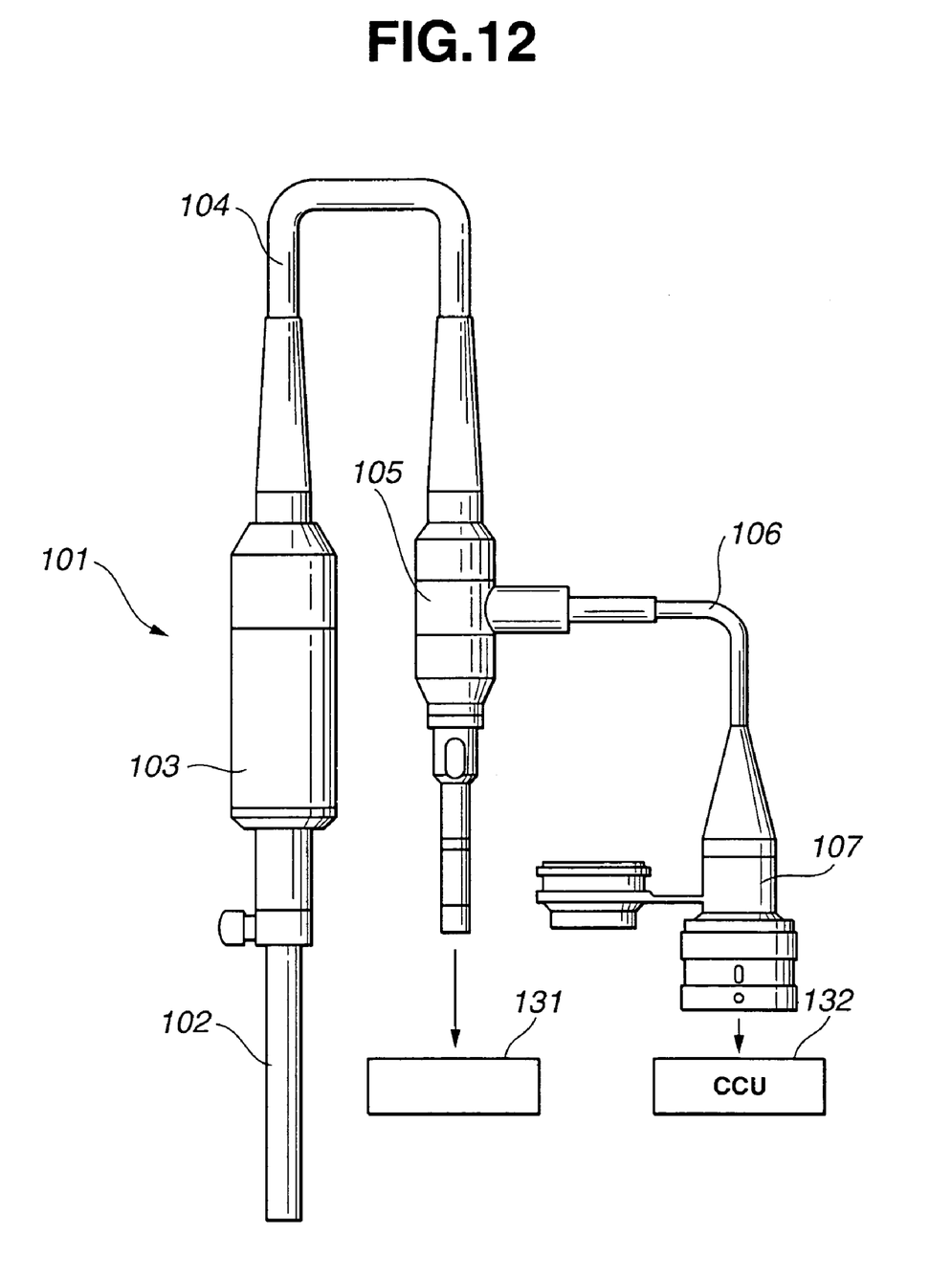
FIG. 12 is an illustrative diagram showing the constitution of an electronic endoscope according to a fourth embodiment of the present invention.
Figure 13:
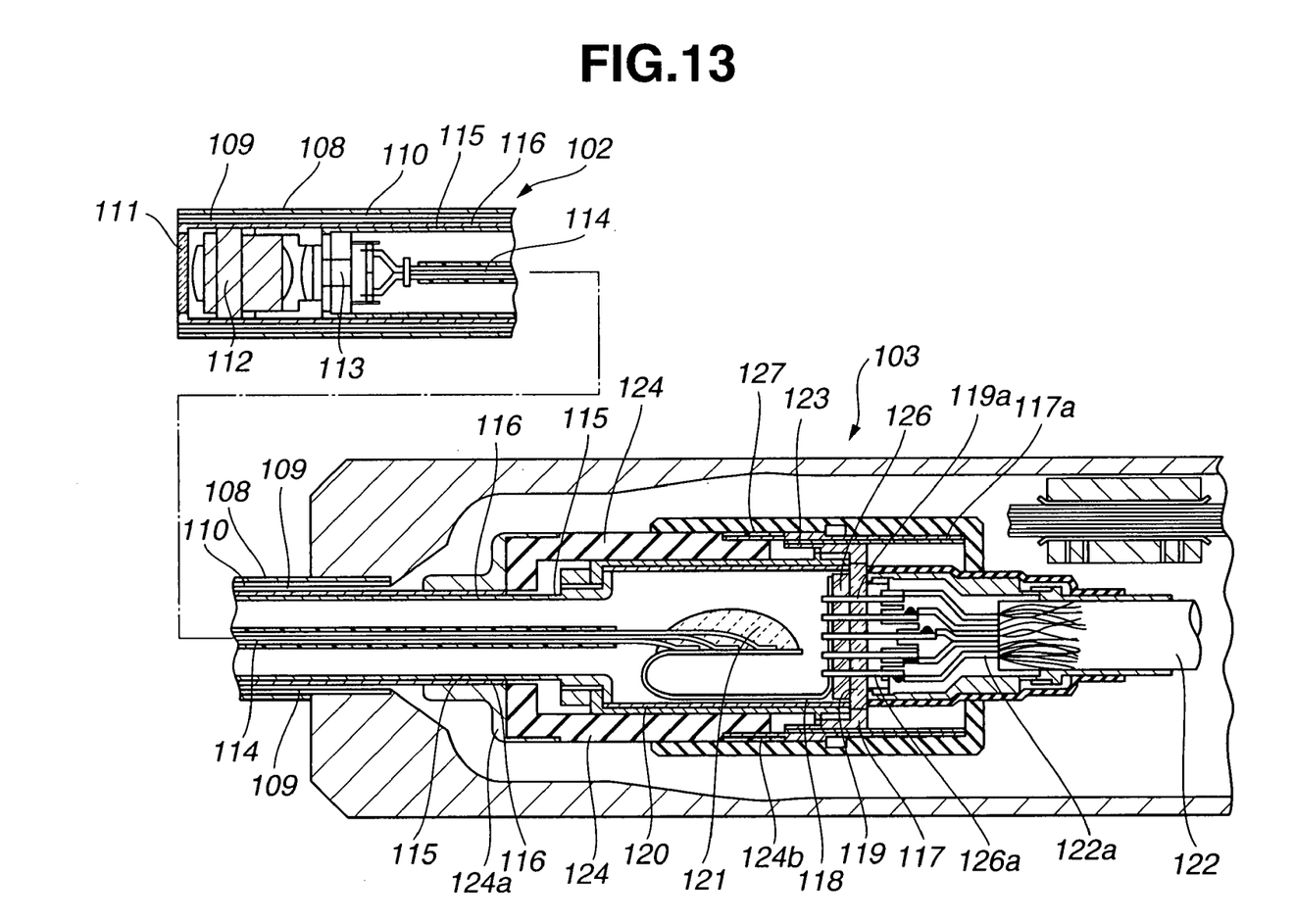
FIG. 13 is a sectional view showing the constitution of an operating portion and an insertion portion of the electronic endoscope according to the fourth embodiment of the present invention.

Next, an image pick-up device according to a fourth embodiment of the present invention will be described using FIGS. 12 and 13. FIG. 12 is an illustrative view showing the overall constitution of an electronic endoscope according to the fourth embodiment of the present invention. FIG. 13 is an enlarged sectional view showing an operating portion and an insertion portion of the electronic endoscope according to the fourth embodiment of the present invention.

As shown in FIG. 12, an electronic endoscope 101 of the fourth embodiment is constituted of an insertion portion 102 which is inserted into a body cavity, an operating portion 103 which is connected to the insertion portion 102 and held by an operator, a universal cord 104, the base end portion of which is connected to the operating portion 103, and the interior of which is inserted with a signal line, a light guide, and so on, a light guide connector (to be referred to as "LG connector" below) 105 which is provided on the tip end portion of the universal cord 104 and connected to a light source device 131, a camera cable 106 which extends from a side portion of the LG connector 105 and through which a signal line from the universal cord 104 passes, a camera connector 107 provided on the tip end portion of the camera cable 106 and connected to a camera control unit (to be referred to as "CCU" below) 132, and so on.

As shown in FIG. 13, the insertion portion 102 of the electronic endoscope 101 is formed of a substantially tubular double pipe constitution comprising two tubes, an outer tube 108 and an inner tube 109. A light guide fiber (to be referred to as "LG fiber" below) 110 for transmitting illumination light is provided between the outer tube 108 and inner tube 109.

The inner tube 109 is metallic. A cover glass 111 is provided on the front end face of the inner tube 109. The outer peripheral surface of the cover glass 111 is coated with metal, and joined to the inner peripheral surface of the inner tube 109 by joining means such as soldering, for example. Thus the inner peripheral surface of the front end portion of the inner tube 109 and the outer peripheral surface of the cover glass 111 are joined hermetically, and the front end side of the inner tuber 109 is hermetically sealed.

An object lens group 112 serving as an object optical system formed of a plurality of optical lenses or the like, and an image pick-up device such as a charge coupled device (to be referred to as "CCD" below) 113 serving as image pick-up means for converting optical images captured inside the body cavity into electrical signals in the position at which images are formed by the object lens group 112 are provided on the optical axis of the cover glass 111 inside the insertion portion 102.

A signal line 114 serving as signal transmission means for transmitting electrical signals is connected to the CCD 113. The signal line 114 extends to the operating portion 103, and the terminal end portion thereof is connected to a flexible printed card (to be referred to as "FPC" below) 118 inside the operating portion 103 to be described below.

The CCD 113 and signal line 114 are covered by a shield member 115 serving as shielding means, the periphery of which is constituted of a substantially tubular metallic member. The CCD 113 and signal line 114 are shielded from electromagnetic waves and the like by the shield member 115. Note that the shield member 115 is connected to a shield member 127 which is provided in the operating portion 103 to be described below.

The outer peripheral surface of the shield member 115 is covered by a heat-shrinkable tube 116 serving as insulation means, and thus the shield member 115 and inner tube 109 are insulated from each other.

The FPC 118 is provided in the interior of the operating portion 103 and connected to the signal line 114. The connection portion is covered and sealed by a sealing member 121 with an insulating property. The FPC 118 is fixed by adhesion in a predetermined position on an insulating plate 126 on which contact pins 126a constituted by a plurality of conductive pin shafts for transmitting electric signals from the signal line 114 are provided, and is electrically wired to the contact pins 126a by soldering or the like.

Further, a substrate frame 117 forming a partition wall is connected to the rear end portion of the shield member 127 which is connected to the shield member 115 from the insertion portion 102. A transparent substrate 119 constituted by a transparent material is hermetically joined to the inner peripheral surface of the substrate frame 117. Metallization is performed on the inner peripheral surface of the substrate frame 117 and outer peripheral surface of the transparent substrate 119, whereupon the two components are hermetically joined by soldering or the like.

A large number of holes 119a is provided in the transparent substrate 119. A surface coating of nickel, gold, or the like is applied around these holes 119a such that the holes 119a can be connected by soldering. The contact pins 126a, which are inserted into and fixed to the FPC 118 and insulating plate 126 from the tip end side thereof, are inserted into the holes 119a of the transparent substrate 119. The contact pins 126a and the surface coating around the holes 119a are soldered together and thus connected hermetically.

A plurality of signal lines 122a of a signal cable 122 serving as signal transmission means are connected respectively to the other end portion of the contact pins 126a extending from the rear face side of the transparent substrate 119. The signal cable 122 is inserted through the camera connector 107.

Thus if the camera connector 107 is connected to the connector portion of the CCU 132, electric signals outputted from the CCD 113 can be transmitted to the CCU 132.

The outer peripheral side of the substrate frame 117 is covered by a thin tubular portion 117a. The tubular portion 117a is fitted onto the inner peripheral surface of a connecting member 123 constituted by a thin, tubular metallic member. By soldering the entire circumference of the fitted portion between the connecting member 123 and tubular portion 117a, the rear end side of the inner tube 109 is hermetically sealed.

Note that hermetic sealing may be performed using joining means such as brazing or laser welding instead of soldering.

A tubular heat-resistant insulating member 124 formed of a ceramic or the like is interposed between the inner tube 109 and connecting member 123. This heat-resistant insulating member 124 insulates the inner tube 109 from the connecting member 123 and substrate frame 117.

A metallic coating is applied respectively to the joint portion 124a between the heat-resistant insulating member 124 and inner tube 109 and the joint portion 124b between the heat-resistant insulating member 124 and connecting member 123, whereupon the components of the respective joint portions 124a and 124b are joined by soldering or the like and thus hermetically sealed.

Electric image signals captured by the CCD 113 inside the insertion portion 102 of the electronic endoscope 101 constituted in this manner are transmitted to the CCU 132 via the signal line 114, FPC 118, contact pins 126a, and the signal lines 122a of the cable 122.

The object lens group 112 and CCD 113 provided in the insertion portion 102 of the electronic endoscope 101 are completely sealed by the airtight space formed by the cover glass 111 on the front end face of the insertion portion 102, the inner tube 109, the heat-resistant insulating member 124, the connecting portion 123, the substrate frame 117, the transparent substrate 119, and so on.

Thus during autoclave sterilization of the electronic endoscope 101, high-pressure, high-temperature water vapor or the like which infiltrates through gaps between each of the signal lines and so on is completely blocked by this airtight space.

Further, a worker can easily insert the contact pins 126a attached to the insulating plate 126 into the holes 119a in the transparent substrate 119, which is joined in advance to the substrate frame 117 constituted by a laser-weldable metal, from the rear side while viewing the operation through the transparent substrate 119. As a result, the assembly operation improves in efficiency.

Note that in the descriptions of each embodiment of the present invention, an endoscope with a flexible insertion portion has been used as a main example, but the present invention may also be applied to a rigid endoscope having a rigid insertion portion.

The present invention may also be used for a camera head attached to an eyepiece portion of the operating portion of an endoscope.

Further, the transparent substrate provided in the vicinity of the solid-state image pick-up device may be constituted as a member for transmitting electric signals or a member for connecting cable to cable.

What is claimed is:

1. An image pick-up device comprising:
    an image pick-up unit for capturing an optical image obtained from incident light entering an internal cavity formed by a frame having an inner surface and an outer surface, and outputting an image signal of the optical image;
    wiring extending from the image pick-up unit in an opposite direction to the direction in which the incident light enters, the wiring being capable of transmitting the image signal; and
    a substrate disposed in a predetermined position within the internal cavity of the frame so as to hermetically seal one of a first opening and a second opening formed on the frame, the substrate having engaging portions for engaging with the wiring, one surface of the substrate being substantially orthogonal to the axial direction of the frame, and formed of a member having a light-transmitting property.

2. The image pick-up device according to claim 1, wherein the engaging portions are holes into which the wiring can be inserted.

3. The image pick-up device according to claim 1, wherein wiring patterns are provided on the surface of the substrate on a proximal face for electrically connecting the engaging portions to the wiring.

4. The image pick-up device according to claim 1, wherein the substrate is joined hermetically to the inner surface of the frame by soldering.

5. An image pick-up device comprising:
    image pick-up means for capturing an optical image obtained from incident light entering an internal cavity formed by a frame, and outputting an image signal of the optical image;
    wiring means extending from the image pick-up means in an opposite direction to the direction in which the incident light enters, which are capable of transmitting the image signal; and
    a substrate disposed in a predetermined position within the internal cavity of the frame so as to hermetically seal one of a first opening and a second opening formed on the frame, the substrate having engaging portions for engaging with the wiring means, one surface of the substrate being substantially orthogonal to the axial direction of the frame, and formed of a member having a light-transmitting property.

6. An endoscope having an insertion portion which can be inserted into a body to be examined, comprising:
    an image pick-up unit for capturing an optical image obtained from incident light entering an internal cavity formed by a frame provided on a front end portion of the insertion portion, and outputting an image signal of the optical image;
    wiring extending from the image pick-up unit in an opposite direction to the direction in which the incident light enters, which is capable of transmitting the image signal; and
    a substrate disposed in a predetermined position within the internal cavity of the frame so as to hermetically seal one of a first opening and a second opening formed on the frame, the substrate having engaging portions for engaging with the wiring, one surface of the substrate being substantially orthogonal to the axial direction, of the frame, and formed of a member having a light-transmitting property.

7. The endoscope according to claim 6, wherein the engaging portions are holes into which the wiring can be inserted.

8. The endoscope according to claim 6, wherein wiring patterns are provided on the surface of the substrate on a proximal face for electrically connecting the engaging portions to the wiring.

9. The endoscope according to claim 6, wherein the substrate is joined hermetically to an inner surface of the frame by soldering.

10. An endoscope having an insertion portion which can be inserted into a body to be examined, comprising:
    image pick-up means for capturing an optical image obtained from incident light entering an internal cavity formed by a frame provided on a front end portion of the insertion portion, and outputting an image signal of the optical image;
    wiring means extending from the image pick-up means in an opposite direction to the direction in which the incident light enters, the wiring means being capable of transmitting the image signal; and a substrate disposed in a predetermined position within the internal cavity of the frame so as to hermetically seal one of a first opening and a second opening formed on the frame, the substrate having engaging portions for engaging with the wiring means, one surface of the substrate being substantially orthogonal to the axial direction of the frame, and formed of a member having a light-transmitting property.

11. An assembly method for an image pick-up device comprising an image pick-up unit for capturing an optical image obtained from incident light and outputting an image signal of the optical image, comprising the steps of:

disposing a substrate formed of a transparent member on the rear end of an internal cavity of a substrate frame such that one surface thereof is substantially orthogonal to an axial direction of the substrate frame, and hermetically joining an inner peripheral surface of the substrate frame and an outer peripheral surface of the substrate;

engaging wiring of a solid-state image pick-up device provided in the image pick-up unit, which extends in an opposite direction to the direction in which the incident light enters, with a plurality of first engaging portions provided in the substrate while performing position alignment visually;

joining the engaging portions and wiring hermetically;

joining the inner surface of the substrate frame and an outer surface of a lens holder of the image pick-up unit hermetically;

engaging cable signal lines inserted into the cable holder with a plurality of second engaging portions in the substrate from an opposite direction to the direction in which the plurality of first engaging portions are engaged with the substrate; and joining the plurality of second engaging portions and the cable signal lines hermetically.

12. The assembly method for an image pick-up device according to claim 11, wherein the plurality of first engaging portions and plurality of second engaging portions are holes into which the wiring and the cable signal lines can be respectively inserted.

13. The assembly method for an image pick-up device according to claim 11, wherein the substrate comprises wiring patterns for electrically connecting the plurality of first engaging portions and the plurality of second engaging portions on the surface of the substrate on a side at which the cable signal lines are engaged with the substrate.

14. The assembly method for an image pick-up device according to claim 11, wherein the substrate is hermetically joined to an inner surface of the substrate frame by brazing.

15. The assembly method for an image pick-up device according to claim 11, wherein wiring is hermetically joined to the plurality of first engaging portions and the cable signal lines are hermetically joined to the plurality of second engaging portions by brazing.

16. An assembly method for an image pick-up device comprising an image pick-up unit for capturing an optical image obtained from incident light and outputting an image signal of the optical image, comprising the steps of:

engaging cable signal lines inserted into a cable holder with a plurality of first engaging portions provided on a substrate formed of a transparent member;

joining the engaging portions and cable signal lines hermetically;

disposing the substrate on a rear end of a substrate frame such that one surface thereof is substantially orthogonal to an axial direction of the substrate frame, and hermetically joining an inner surface of the substrate frame and an outer surface of the substrate;

engaging wiring of a solid-state image pick-up device provided in the image pick-up unit, which extends in an opposite direction to the direction in which the incident light enters, with a plurality of second engaging portions provided in the substrate while performing position alignment visually;

joining the plurality of second engaging portions and wiring hermetically; and joining the inner peripheral surface of the substrate frame and an outer surface of a lens holder of the image pick-up unit hermetically.

17. The assembly method for an image pick-up device according to claim 16, wherein the plurality of first engaging portions and plurality of second engaging portions are holes into which the wiring and the cable signal lines can be respectively inserted.

18. The assembly method for an image pick-up device according to claim 16, wherein the substrate comprises wiring patterns for electrically connecting the plurality of first engaging portions and plurality of second engaging portions on the surface of the substrate on the side at which the cable signal lines are engaged with the substrate.

19. The assembly method for an image pick-up device according to claim 16, wherein the substrate is hermetically joined to the inner surface of the substrate frame by brazing.

20. The assembly method for an image pick-up device according to claim 16, wherein wiring is hermetically joined to the plurality of first engaging portions and the cable signal lines are hermetically joined to the plurality of second engaging portions by brazing.

* * * * *